US007972358B2

(12) United States Patent
Nielsen et al.

(10) Patent No.: US 7,972,358 B2
(45) Date of Patent: Jul. 5, 2011

(54) APPARATUS FOR SEALING A PUNCTURE BY CAUSING A REDUCTION IN THE CIRCUMFERENCE OF THE PUNCTURE

(75) Inventors: Stevan Nielsen, Rottenberg (DE); Bodo Quint, Rottenberg (DE); Randolf Von Oepen, Los Altos Hills, CA (US); Kenneth J. Michlitsch, Livermore, CA (US); Gerd Seibold, Ammerbuch (DE); Tommy Conzelmann, Rangendingen (DE); Ib Erling Joergensen, Haigerloch (DE)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 1329 days.

(21) Appl. No.: 10/523,218

(22) PCT Filed: Jul. 25, 2003

(86) PCT No.: PCT/EP03/08247
§ 371 (c)(1),
(2), (4) Date: Oct. 19, 2005

(87) PCT Pub. No.: WO2004/012605
PCT Pub. Date: Feb. 12, 2004

(65) Prior Publication Data
US 2006/0155319 A1 Jul. 13, 2006

Related U.S. Application Data

(60) Provisional application No. 60/401,173, filed on Aug. 1, 2002.

(51) Int. Cl.
*A61B 17/08* (2006.01)
*A61B 17/34* (2006.01)

(52) U.S. Cl. .................. 606/213; 606/216; 606/186
(58) Field of Classification Search .............. 606/186, 606/185, 184, 167, 213, 222, 223, 214, 216; 600/29, 30; 604/41, 164.01
See application file for complete search history.

(56) References Cited

U.S. PATENT DOCUMENTS

| 3,572,336 A * | 3/1971 | Hershberg ............... 604/136 |
| 3,625,793 A * | 12/1971 | Sheridan et al. .......... 156/229 |
| 4,392,493 A | 7/1983 | Niemeijer |
| 4,863,437 A * | 9/1989 | Clarke ...................... 604/246 |
| 5,049,141 A * | 9/1991 | Olive ........................ 604/891.1 |
| 5,061,274 A | 10/1991 | Kensey |
| 5,275,616 A * | 1/1994 | Fowler ...................... 606/213 |

(Continued)

FOREIGN PATENT DOCUMENTS

CA 2424175 4/2002

(Continued)

OTHER PUBLICATIONS

U.S. Appl. No. 60/401,173, filed Aug. 1, 2002, Nielsen.

(Continued)

*Primary Examiner* — (Jackie) Tan-Uyen T Ho
*Assistant Examiner* — Jing Rui Ou
(74) *Attorney, Agent, or Firm* — Workman Nydegger (57) ABSTRACT

Apparatus is provided for sealing a vascular puncture by causing a reduction in the circumference of the puncture tract through delivery of a closure agent into tissue surrounding the puncture tract. A resultant inflammatory response and volumetric increase cause the tissue to swell into the puncture tract, thereby sealing it.

18 Claims, 10 Drawing Sheets

U.S. PATENT DOCUMENTS

| | | | |
|---|---|---|---|
| 5,728,114 A * | 3/1998 | Evans et al. | 606/148 |
| 5,830,125 A * | 11/1998 | Scribner et al. | 606/139 |
| 5,868,762 A | 2/1999 | Cragg et al. | |
| 6,120,786 A * | 9/2000 | Cherif Cheikh | 424/426 |
| 6,251,063 B1 | 6/2001 | Silverman et al. | |
| 6,302,870 B1 * | 10/2001 | Jacobsen et al. | 604/272 |
| 6,391,048 B1 | 5/2002 | Ginn et al. | |
| 6,663,647 B2 * | 12/2003 | Reiley et al. | 606/192 |
| 6,692,466 B1 * | 2/2004 | Chow et al. | 604/164.01 |
| 6,835,193 B2 * | 12/2004 | Epstein et al. | 604/507 |
| 7,008,439 B1 * | 3/2006 | Janzen et al. | 606/213 |
| 7,179,266 B2 * | 2/2007 | Kontos | 606/144 |
| 7,291,129 B2 * | 11/2007 | Li et al. | 604/164.01 |
| 2002/0045928 A1 * | 4/2002 | Boekstegers | 623/1.11 |
| 2002/0082546 A1 * | 6/2002 | Crank et al. | 604/48 |
| 2002/0123740 A1 * | 9/2002 | Flaherty et al. | 604/890.1 |
| 2002/0143291 A1 * | 10/2002 | Slater | 604/95.01 |
| 2003/0028172 A1 * | 2/2003 | Epstein et al. | 604/507 |

FOREIGN PATENT DOCUMENTS

| | | |
|---|---|---|
| WO | WO89/11301 | 11/1989 |
| WO | WO 8911301 A | 11/1989 |
| WO | WO96/35464 | 11/1996 |
| WO | WO97/09934 | 3/1997 |
| WO | WO98/31286 | 7/1998 |
| WO | WO 9831286 A | 7/1998 |
| WO | WO2004/012605 | 2/2004 |

OTHER PUBLICATIONS

U.S. Appl. No. 60/400,658, filed Jul. 31, 2002, Seibold, et al.

* cited by examiner

APPARATUS FOR SEALING A PUNCTURE BY CAUSING A REDUCTION IN THE CIRCUMFERENCE OF THE PUNCTURE

FIELD OF THE INVENTION

The present invention relates to apparatus for sealing punctures. More specifically, the invention relates to apparatus that may be percutaneously inserted to seal a puncture by causing a reduction in the circumference of the puncture.

BACKGROUND OF THE INVENTION

A large number of medical diagnostic and therapeutic procedures involve percutaneous introduction of instrumentation into a blood vessel. For example, coronary angioplasty, angiography, atherectomy, stenting, and numerous other procedures often involve accessing the vasculature through placement of a catheter or other device in a patient's femoral artery or other blood vessel. Once the procedure is completed and the catheter or other diagnostic or therapeutic device is removed, bleeding from the resultant vascular puncture must be stopped.

Traditionally, a medical practitioner applies external pressure to the percutaneous entry site to stem bleeding until hemostasis has occurred (i.e. when the clotting and tissue rebuilding have sealed the puncture). This method, however, presents numerous problems. In some instances, this pressure must be applied for up to an hour or more during which time the patient is uncomfortably immobilized. In addition, there exists a risk of hematoma, since bleeding from the puncture may continue until sufficient clotting affects hemostasis. Furthermore, application of external pressure to stop bleeding may be unsuitable for patients with substantial amounts of subcutaneous adipose tissue, because the skin surface may be a considerable distance from the puncture site, thereby rendering external compression less effective.

Another traditional approach to subcutaneous puncture closure involves internally suturing the vessel puncture. This method, however, comprises a complex process and requires considerable skill by the medical practitioner.

Mechanical occlusion devices have been proposed for sealing vascular punctures in U.S. Provisional Patent Application Ser. No. 60/400,658, filed Jul. 31, 2002, which describes a closure device having two expandable disks that sealingly compress a vessel or tissue surrounding the puncture site. Advantageously, the two disks may be repositioned post-deployment at the puncture without inflicting additional trauma to the engaged vessel or tissue.

Apparatus and methods also are known in which a plug is introduced into the vessel puncture, to cover the puncture and promote hemostasis. Various types of plugs have been proposed. One example is described in U.S. Pat. No. 5,061,274 to Kensey, comprising a plug made from animal-derived collagen. Such a plug inserted into the puncture may be dislodged into the vessel during the healing process due to the application of pressure to the wound, potentially causing stenosis of the vessel. Furthermore, the presence of the plug within the puncture prevents re-access to the puncture site without potentially dislodging the plug into the vessel. Further still, there is a risk of unwanted adverse reaction to the animal-derived collagen.

In view of the drawbacks associated with prior art methods and apparatus for sealing a vascular puncture, it would be desirable to provide apparatus that overcomes such drawbacks.

It would be desirable to provide apparatus for sealing a vascular puncture by inducing a reduction in the circumference of the puncture.

It also would be desirable to provide apparatus for sealing a vascular puncture that reduces a potential that a portion of a wound closure device will protrude into the vessel lumen.

It further would be desirable to provide apparatus for sealing a vascular puncture that is easy to use.

It even further would be desirable to provide apparatus for sealing a vascular puncture that permits re-access to the puncture site.

It still further would be desirable to provide apparatus for sealing a vascular puncture that are biodegradable.

SUMMARY OF THE INVENTION

In view of the foregoing, it is an object of the present invention to provide apparatus for sealing a vascular puncture by inducing a reduction in the circumference of the puncture.

It also is an object of the present invention to provide apparatus for sealing a vascular puncture that reduces a potential that a portion of a wound closure device will protrude into the vessel lumen.

It further is an object of the present invention to provide apparatus for sealing a vascular puncture that is easy to use.

It even further is an object of the present invention to provide apparatus for sealing a vascular puncture that permits re-access to the puncture site.

It still further would be desirable to provide apparatus for sealing a vascular-puncture that are biodegradable.

These and other objects of the present invention are accomplished by providing apparatus for sealing a vascular puncture by delivering an agent into tissue surrounding a puncture tract that induces a reduction in the circumference of the puncture and puncture tract. More specifically, the apparatus of the present invention induces reduction of the puncture diameter by delivering a closure agent into tissue immediately surrounding the puncture tract to cause the tissue to swell into and seal the puncture tract. The closure agent may comprise a water swellable gel, collagen, a saline bolus, a granular slurry, an inflammatory substance, and/or a plurality of balloons.

A first embodiment of apparatus of the present invention comprises a housing having a plurality of needles, and optionally, a shaft having an expandable member disposed on its distal end. When expanded, the expandable member engages an inner vessel surface distal to the puncture. The proximal force transmitted by the expandable member stabilizes the vessel wall and surrounding tissue during insertion of the needles.

An optional injection manifold may be fluidically coupled to an injection port and the plurality of needles. An actuator coupled to the injection manifold may be operable to cause the plurality of needles to penetrate into the subcutaneous tissue surrounding the puncture tract in a direction generally parallel to the puncture tract.

In accordance with one aspect of the present invention, the injection apparatus also comprises a stop to limit distal advancement of the plurality of needles into the tissue surrounding the puncture tract. In a preferred embodiment, this may be associated with the position of the expandable member in the puncture tract.

In an alternative embodiment of the present invention, apparatus may be provided comprising a housing coupled to a plurality of needles that have lengths shorter than that of the puncture tract, or that are constrained such that a depth to which they may penetrate tissue is not greater than the length of the puncture tract. Preferably, the housing is annular in shape and the plurality of needles are circumferentially arrayed. However, other configurations also are within the scope of the present invention. The apparatus is preferably configured such that the housing limits a depth to which the needles may be advanced into the patient's tissue by abutting the exterior of the patient, i.e. abutting the patient's skin, when the needles have been translated to their maximum depth proximal of the vessel. This reduces a risk of inadvertent insertion of the needles into vessel V.

The apparatus optionally comprises a centering shaft configured for placement in the puncture tract. The plurality of needles may be advanced in unison with the centering shaft into the tissue and puncture tract, respectively, or may be advanced over the centering shaft after the centering shaft is already disposed within the puncture tract. This ensures that the plurality of needles is centered about the puncture tract and thereby accurately punctures tissue surrounding the puncture tract.

BRIEF DESCRIPTION OF THE DRAWINGS

Further features of the present invention, its nature and various advantages will be more apparent from the accompanying drawings and the following detailed description of the preferred embodiments, in which.

DETAILED DESCRIPTION OF THE INVENTION

Figure 1:
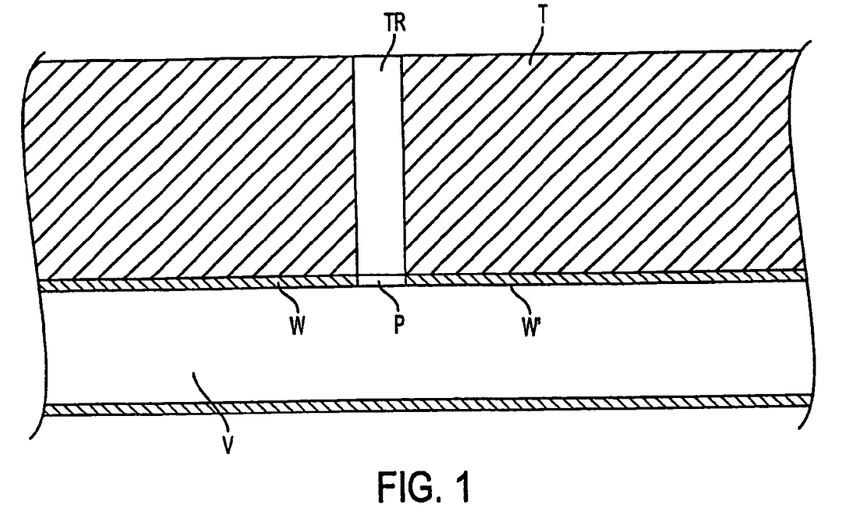
FIG. 1 is a schematic side-sectional view of a vascular puncture tract.

Upon completion of a medical diagnostic or therapeutic procedure involving percutaneous introduction of instrumentation into blood vessel V, removal of the instrumentation from the patient leaves puncture tract TR. As seen in FIG. 1, puncture tract TR extends through subcutaneous tissue T and vessel wall W, and terminates at puncture P. The apparatus of the present invention is directed to a device for sealing puncture P by causing a reduction in the circumference of the puncture and puncture tract. Specifically, the device of the present invention involves delivering a closure agent into tissue T immediately surrounding puncture tract TR to cause tissue T to swell into and seal puncture tract TR.

In a preferred embodiment of the present invention, the closure agent comprises a biodegradable substance that may be delivered in a fluid state, and that swells or increases in volume in the presence of water. A continual increase in the volume of the closure agent, when disposed within the tissue surrounding puncture tract TR, causes a consequent swelling of the tissue that decreases the circumference of puncture P until the puncture is closed.

One example of a closure agent suitable for use with the apparatus of the present invention is a hydrogel. A number of synthetic and animal-based hydrogels are known in the art.

Alternatively, the closure agent may comprise an inflammatory substance. Injection of the inflammatory substance into tissue T surrounding puncture tract TR causes a narrowing of the puncture by initiating a localized inflammation response in tissue T due to the presence of the inflammatory substance, thereby causing localized swelling that decreases the circumference of puncture tract TR and puncture P until the puncture is closed.

One example of an inflammatory substance that may be used is copper sulfate. Described in *The Merck Index*, 12$^{th}$ Edition, (Budavari et al., Eds.) Merck Research Laboratories, Whitehouse Station, N.J., 1996, copper sulfate is a strong irritant that is soluble in water. One parameter that indicates the toxicity of copper sulfate is its $LD_{50}$ index, which is defined herein as the amount of a substance that is sufficient to kill 50% of a population of animals. The $LD_{50}$ for copper sulfate, when administered orally to rats, is 960 mg/kg. Thus, when administered in low dosages as a closure agent in accordance with the principles of the present invention, copper sulfate may provide localized inflammation in the area surrounding puncture P, and yet holistically be well tolerated by the patient.

As yet further alternatives, the closure agent may comprise collagen, a bolus of saline, which is resorbed into the tissue, a slurry formed from granules of a biocompatible substance, such as polyglycolic acid, and/or an expandable member, such as one or more inflatable balloons, to be described in greater detail hereinbelow.

Figure 2A:
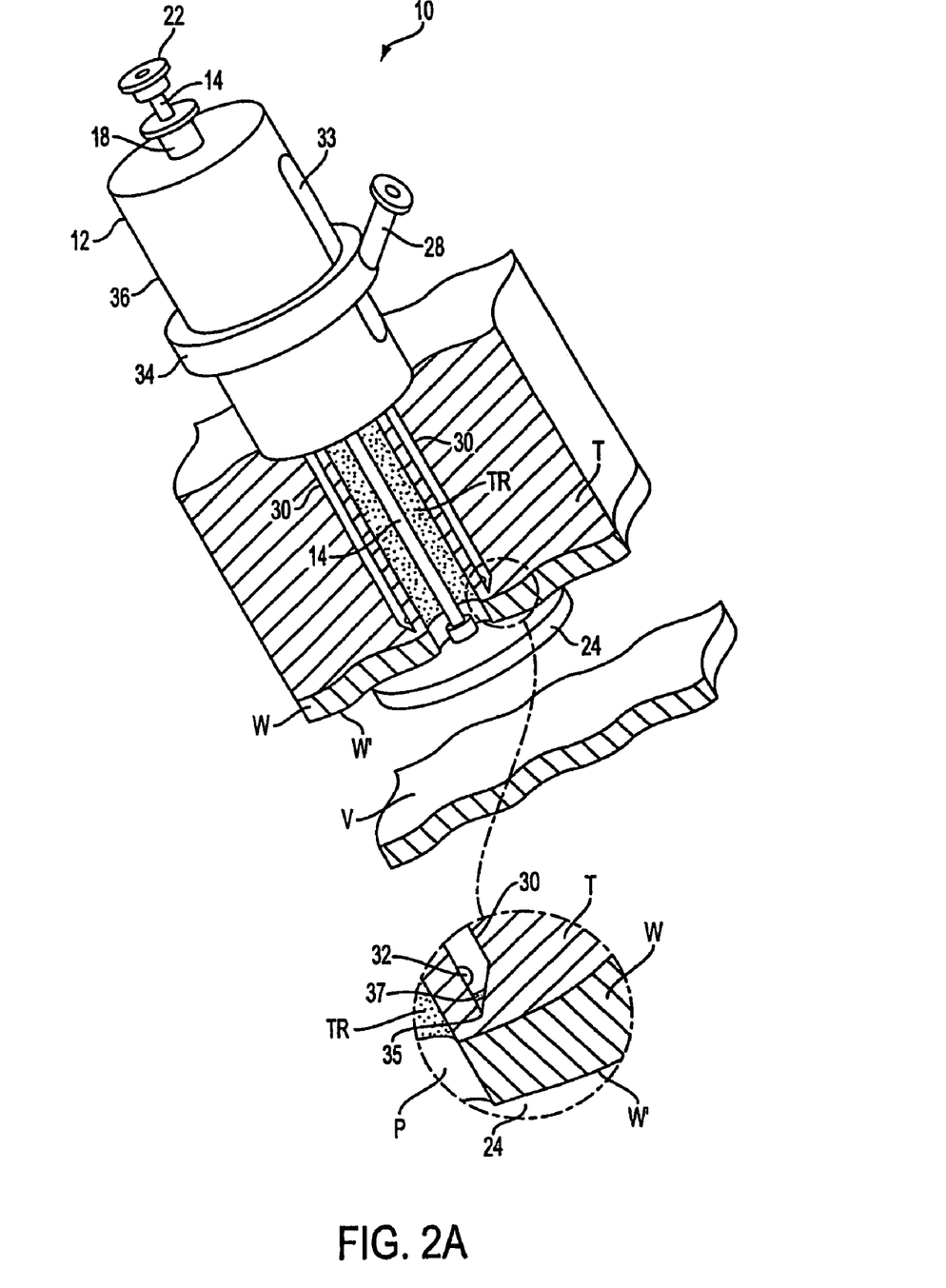
FIG. 2A is a schematic perspective view, partially in section, of apparatus of the present invention deployed to seal the puncture of FIG. 1.
Figure 2B:
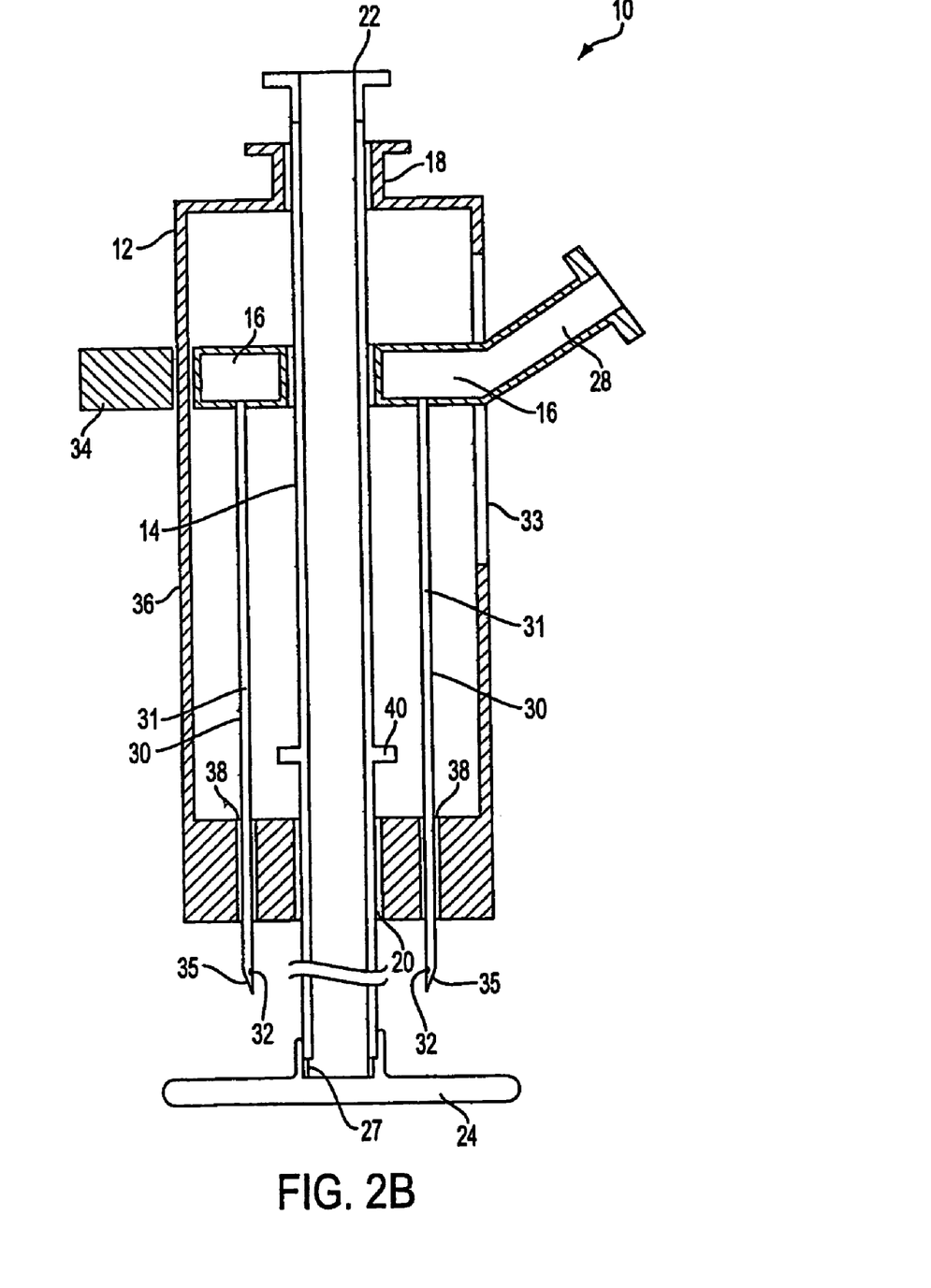
FIG. 2B is a schematic side-sectional view of the apparatus of FIG. 2A.

An illustrative embodiment of device 10 of the present invention is shown in FIGS. 2A and 2B, percutaneously disposed traversing puncture tract TR. Injection device 10 comprises housing 12, shaft 14, and injection manifold 16. Shaft 14 is disposed to be axially translatable with respect to housing 12 through Toughy-Borst valve 18, which is disposed on the proximal end of housing 12, and through distal lumen 20, which is disposed in the distal end of housing 12. Toughy-Borst valve 18 may be actuated to releasably lock shaft 14 to housing 12. Shaft 14 is coupled to port 22, and is used to deploy and retract expandable member 24 disposed on the distal end of shaft 14. Illustratively, expandable member 24 is a disk-shaped balloon, although other structures such as mechanically expandable baskets, pledgets or super-elastic coils may be used. Port 22 may comprise, e.g., a luer valve, and be configured to releasably couple to a standard inflation source (not shown), per se known in the art. In the configuration shown in FIG. 2, expandable member 24 has a diameter greater than the diameter of puncture P. Shaft 14 also may comprise radiopaque band 27 disposed on the distal end of the shaft to provide visual guidance during insertion of apparatus 10 when used with a fluoroscopy system, as is known in the art.

Manifold 16 comprises inlet port 28, and is in fluid communication with plurality of needles 30. As more clearly shown in the inset of FIG. 2A, each needle 30 has injection lumen 31 in fluid communication with manifold 16, at least one injection aperture 32 disposed on the distal end of needle 30, sharp distal tip 35 shaped to penetrate subcutaneous tissue T, and an optional radiopaque marker 37 disposed in the vicinity of distal tip 35. Inlet port 28 may comprise, for example, a luer coupling that may be releasably coupled to a source of closure agent (not shown). Fluid communication among inlet port 28, injection manifold 16, and lumens 31 permits closure agent introduced into inlet port 28 to flow into injection lumens 31, and through apertures 32 into the tissue surrounding the puncture tract. Injection manifold 16 illustratively has an annular shape, and is configured to be disposed around and slide along shaft 14. Inlet port 28 extends from housing 12 through slot 33 and may be coupled to actuator 34 concentrically disposed around lateral wall 36 of housing 12.

Along with inlet port 28, actuator 34 may be used to longitudinally translate manifold 16, subsequently translating needles 30 therewith. Translation of needles 30 is guided by plurality of needle lumens 38 formed in a distal portion of housing 12. The length of slot 33 and the relative position of shaft 14 limit translation of needles 30. Shaft 14 may include flange 40, which serves as a distal stop to limit distal translation of injection manifold 16. Flange 40 is positioned along shaft 14 so that the distance between flange 40 and expandable member 24 is slightly greater than the length of needles 30. Advantageously, this ensures that needles 30 may be disposed within tissue just proximal of vessel wall W to deliver closure agent therein, without piercing vessel wall W. Stop 40 eliminates the need for visual confirmation of the position of needles 30 and apertures 32 prior to injection of the closure agent. Alternatively, if visual confirmation is desired, observation of radiopaque markers 27 and 37 respectively disposed on shaft 14 and needles 30 may be made using conventional fluoroscopic techniques.

It will be evident to one of ordinary skill in the art that apparatus 10 of the present invention may comprise more than the two needles, as shown in the figures, or as few as a single needle. If puncture tract TR and puncture P are substantially circular in shape, additional needles 30 may be disposed to penetrate subcutaneous tissue T so that closure agent may be injected into the tissue surrounding puncture tract TR in a circular pattern. If the puncture tract and the puncture is of another geometry, needles 30 may be configured to penetrate the subcutaneous tissue in a pattern that complements that geometry.

Figure 3:
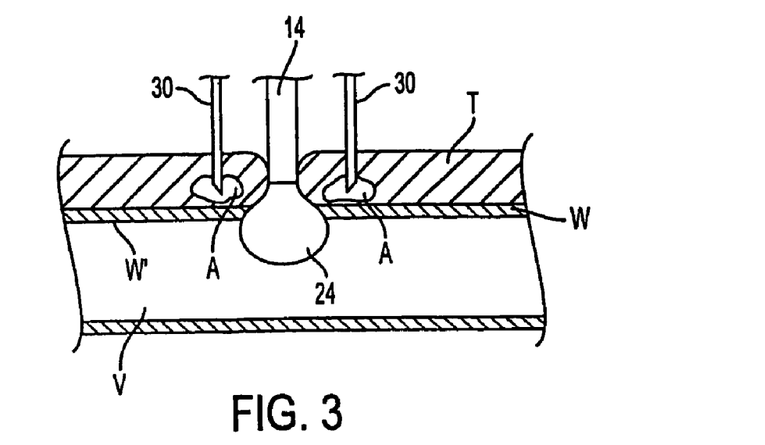
FIG. 3 is a schematic side view, partially in section, of an alternative embodiment of an expandable member of the apparatus of the present invention in its deployed configuration.

In accordance with one aspect of the present invention, expandable member 24 is disk-shaped to provide a substantially flat profile against inner vessel surface W' when deployed and engaged therewith. This flat profile reduces disturbance to blood flow, and, in a manner described in greater detail below, expandable member 24 may deflect vessel wall W to facilitate delivery of the closure agent. In an alternative embodiment, expandable member 24 may comprise a spherical shape, as illustrated in FIG. 3.

Figure 4A:
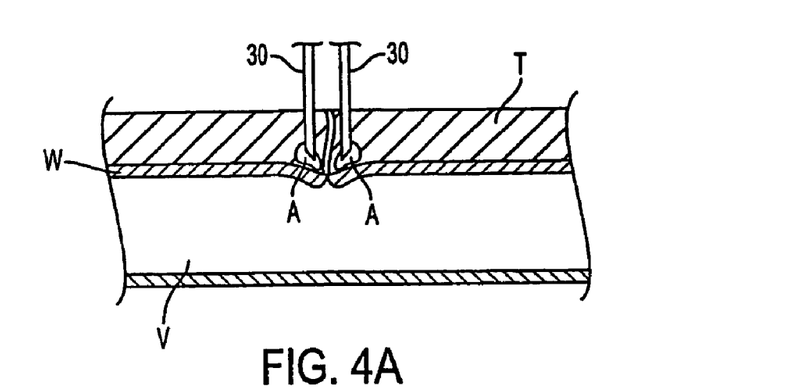
FIGS. 4A and 4B are schematic side views, partially in section, of a plurality of needles of the apparatus of the present invention, the two views illustrating delivery of closure agent to tissue surrounding a puncture tract without and with, respectively, the use of the expandable member of FIG. 3.
Figure 4B:
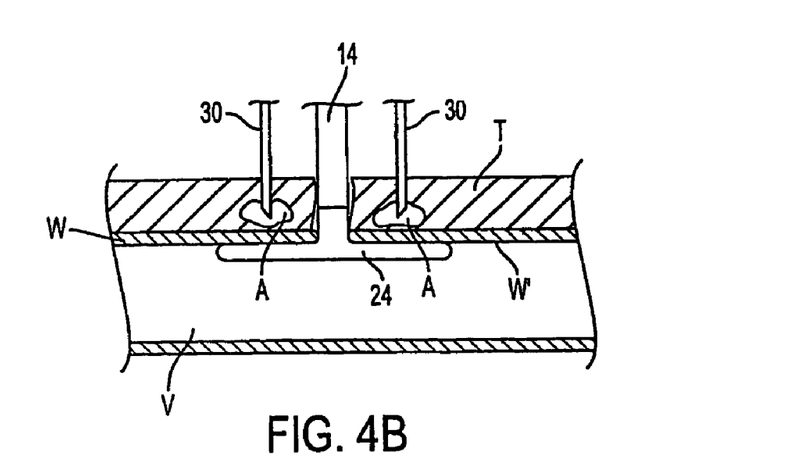
Figure 5A:
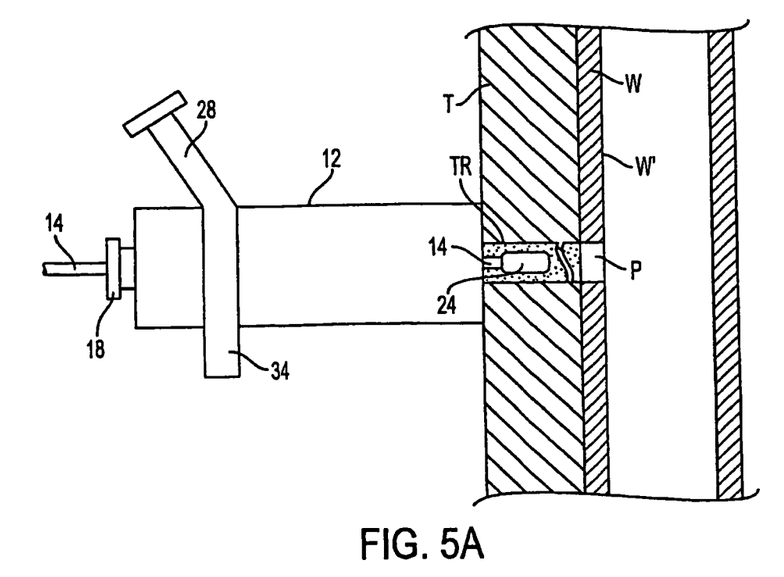
FIGS. 5A-5D are schematic side views, partially in section and/or cut-away, describing an exemplary method of using the apparatus of FIGS. 1-4.
Figure 5B:
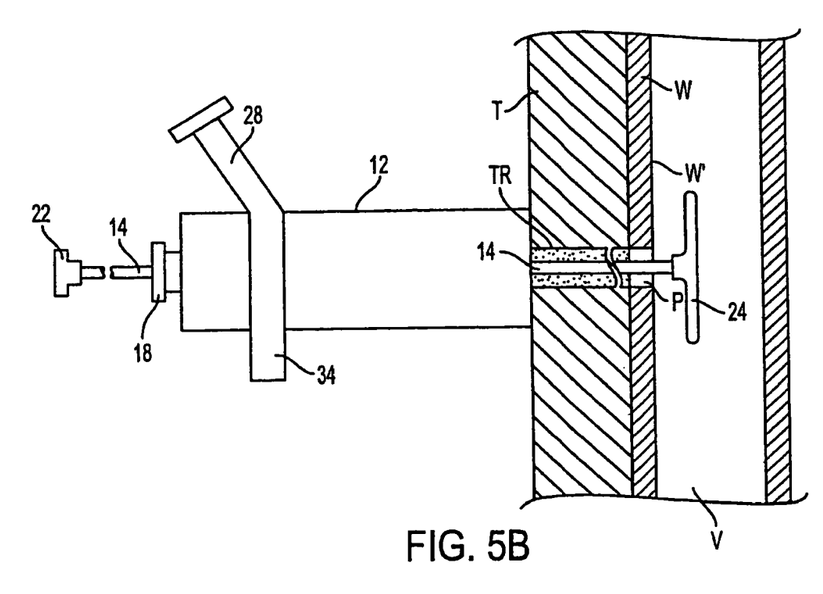
Figure 5C:
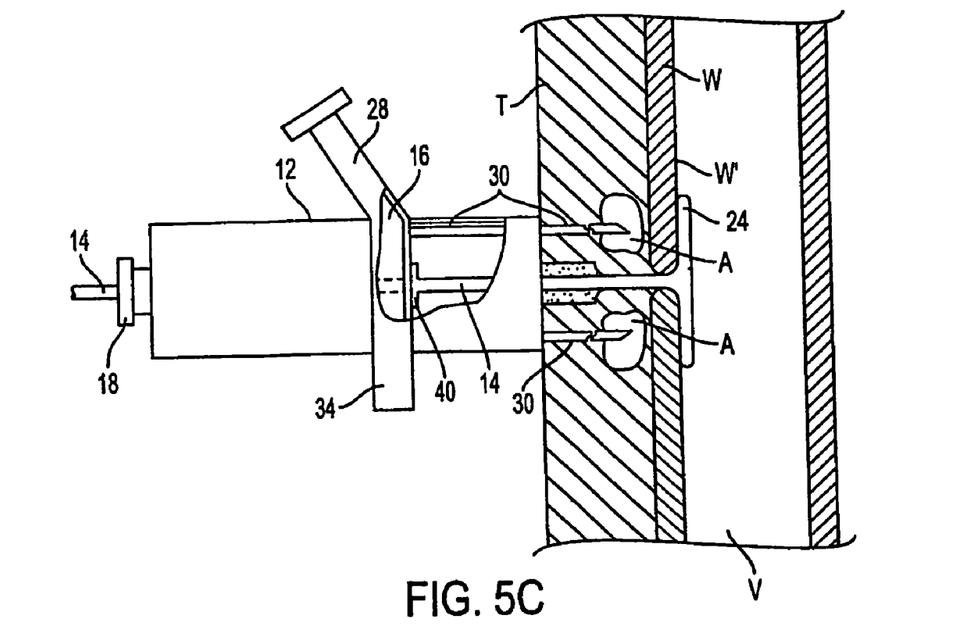
Figure 5D:
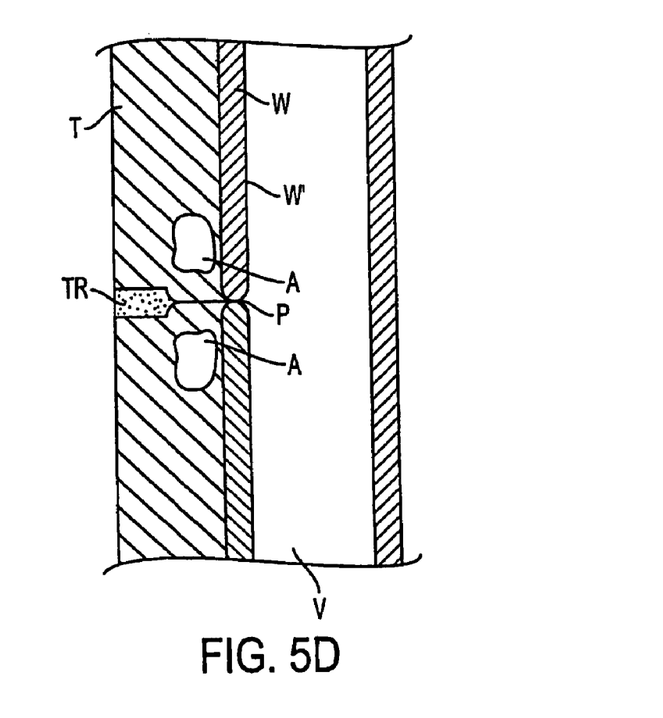

In accordance with another aspect of the present invention, expandable member 24 is expected to reduce "tenting" of tissue T and vessel wall W into the lumen of vessel V. As used herein and shown in FIG. 4A, "tenting" refers to a tendency for tissue T surrounding puncture tract TR and vessel wall W surrounding puncture P to deflect into the lumen of vessel V when the tissue begins to swell after the injection of closure agent A therein. In the present invention, "tenting" of the tissue into the lumen of vessel V may be reduced by application of a proximally directed force to shaft 14, which in turn engages expandable member 24 against inner vessel surface W'. Accordingly, as shown in FIG. 4B, any deflection of tissue T and vessel wall W is directed in the proximal direction away from the lumen of vessel V. This reduces a risk that vessel V at least partially will be occluded from distal protrusion of tissue T and vessel wall W. Furthermore, when expanded and engaged against inner vessel surface W', the proximal force transmitted by expandable member 24 is expected to stabilize the vessel wall and surrounding tissue during insertion of needles 30.

Referring now to FIG. 5, an exemplary method of using apparatus 10 of the present invention is described. First, housing 12 is placed against a patient's skin with distal lumen 20 aligned with puncture tract TR. Alignment may be facilitated if shaft 14 is slightly advanced out of distal lumen 20 so that it may be inserted into puncture tract TR. Shaft 14 then is distally advanced until expandable member 24 is introduced into the lumen of vessel V. This position may be determined by observance of radiopaque band 27 disposed on the distal end of shaft 14, or by tactile feedback.

Once expandable member 24 is disposed within vessel V, expandable member 24 is deployed to its disk-shaped configuration. A proximal force then may be applied to shaft 14 to forcibly engage expandable member 24 against inner vessel surface W', providing immediate hemostasis.

After expandable member 24 is engaged to vessel wall W, Toughy-Borst valve 18 is actuated to lock shaft 14 relative to housing 12, thereby maintaining forcible engagement of expandable member 24 to inner vessel surface W'. This in turn locks the longitudinal position of flange 40 attached to shaft 14, and defines the maximum distal position to which needles 30 may be translated. Advantageously, the maximum distal position of needles 30 is designed to coincide with introduction of needles 30 into tissue surrounding the puncture tract just proximal of vessel wall W. Alternatively, instead of using Toughy-Borst valve 18, a continual proximal force may be applied to shaft 14 to maintain the position of shaft 14 with respect to housing 12.

Injection manifold 16 then may be translated in the distal direction by depressing actuator 34. Since needles 30 are affixed to manifold 16, distal force applied to actuator 34 is transmitted to needles 30, thereby penetrating subcutaneous tissue T with plurality of needles 30. During insertion of needles 30, the proximal force transmitted by expandable member 24 to inner vessel surface W' stabilizes vessel wall W and tissue T. As discussed above, injection manifold 16 may be actuated in the distal direction until manifold 16 contacts flange 40. At this position, needles 30 have penetrated into tissue T just proximal of vessel wall W.

Inlet port 28 then is coupled to a source of closure agent A, such as a syringe (not shown), and the closure agent then is introduced through needles 30 into the tissue surrounding puncture tract TR. Depending on whether a biodegradable substance such as a water swellable gel, an inflammatory substance such as copper sulfate, or a bioresorbable substance such as saline or a slurry, is introduced, puncture tract TR will decrease in circumference as a result of swelling of tissue T from inflammation thereof and/or a volumetric increase. As discussed with respect to FIG. 4, the proximal force applied to vessel wall W from engagement of expandable member 24 to inner vessel surface W' proximally deflects tissue T surrounding puncture tract TR as the tissue swells, thereby reducing a potential that the tissue will protrude into the lumen of vessel V. This imposed force establishes a propensity for any additional swelling of tissue T also to "tent" in the proximal direction even after expandable member 24 is contracted and removed from puncture tract TR.

After tissue T has sufficiently swelled so that blood does not flow from puncture tract TR, expandable member 24 is contracted and disengaged from inner vessel surface W'. Shaft 14 is released from Touhy-Borst valve 18, and a proximally directed force is applied to shaft 14 to retract shaft 14 and expandable member 24 from puncture tract TR. Since injection manifold 16 is in contact with and proximally disposed relative to flange 40, proximal retraction of shaft 14 also retracts needles 30. It should be understood that shaft 14, expandable member 24 and needles 30 may alternatively be removed as soon as closure agent A has been introduced into the tissue surrounding puncture tract TR.

After shaft 14 is removed, the compliancy and continual swelling of tissue T causes the vessel wall to pervade the space formerly occupied by shaft 14 within puncture P and puncture tract TR, thereby sealing the puncture and puncture tract. Any further "tenting" of tissue T and vessel wall W also is expected to deflect in the proximal direction pursuant to the propensity established by the previously applied proximally directed force that engaged expandable member 24 to inner vessel surface W'.

Figure 6A:
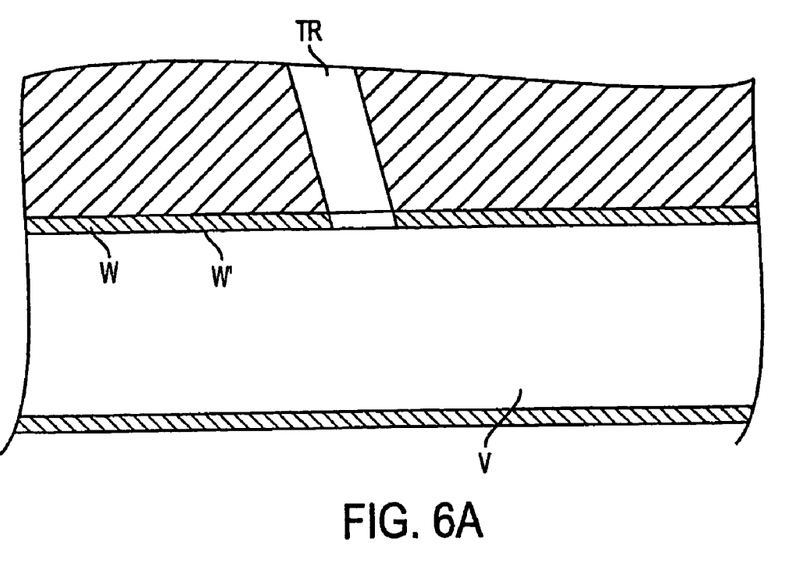
FIGS. 6A and 6B are schematic side views, partially in section, describing an optional step in using the apparatus of FIGS. 1-4.
Figure 6B:
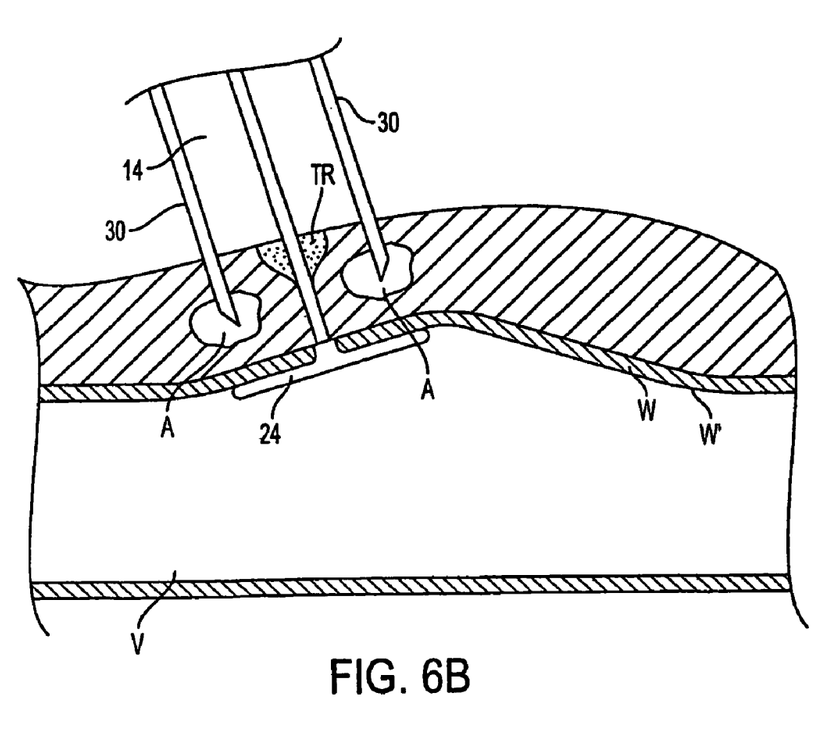

If puncture tract TR is not disposed substantially orthogonal to vessel V, as illustrated in FIG. 6, the proximal force applied to shaft 14 to forcibly engage expandable member 24 against inner vessel surface W' locally may deflect vessel wall W so that the vessel wall in the immediate vicinity of puncture P is disposed substantially orthogonal to puncture tract TR. This configuration ensures that needles 30 do not penetrate into vessel wall W, expandable member 24, or vessel V. Accordingly, expandable member 24 preferably has sufficient strength to locally deflect the vessel wall in the manner shown in FIG. 6B.

Apparatus 10 of the present invention presents numerous advantages over previously known systems. First, in contrast to previously known wound closure devices described above, the present invention significantly reduces a risk that the wound closure device may become dislodged into a lumen of vessel V, because the closure agent is injected directly into tissue T surrounding puncture tract TR, not directly into puncture tract TR. Accordingly, this eliminates a potential mode for a thrombotic or embolic event. Furthermore, the proximally directed force that engages expandable member 24 against inner vessel surface W' establishes a propensity for tissue T and vessel wall W to "tent" in the proximal direction when the tissue swells from the injected closure agent, thereby preventing any protrusion into the lumen of vessel V that may disturb blood flow and serve as a site for thrombosis or embolism.

Moreover, the apparatus of the present invention is expected to permit re-access to the puncture tract since the present invention does not implant any structures therein. Accordingly, other diagnostic or therapeutic devices may be reinserted into puncture tract TR to access vessel V so that additional diagnostic or therapeutic procedures may be performed, thereby eliminating the need to create additional puncture sites.

Figure 7A:
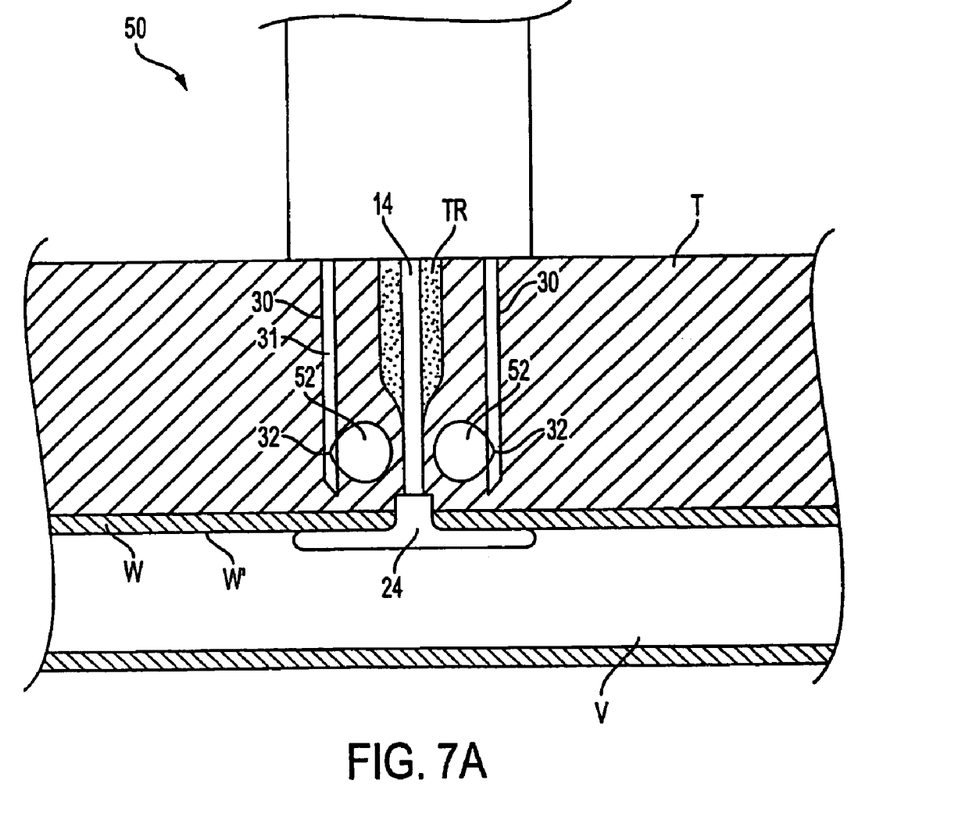
FIG. 7A is a schematic side view, partially in section of an alternative closure agent of the apparatus of FIGS. 1-6.
Figure 7B:
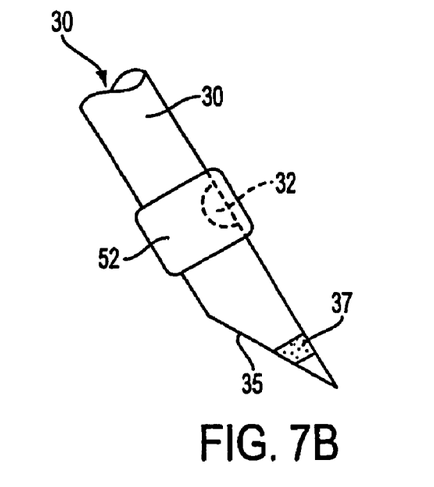
FIG. 7B is a schematic perspective detail view of the closure agent of FIG. 7A.

Referring now to FIGS. 7A-7B, an alternative closure agent for use with device 10 is described. Device 50 is similar to device 10, except for the inclusion of plurality of balloons 52 disposed over apertures 32 in the distal region of needles 30. In the present embodiment, rather than injecting a closure agent directly into tissue T surrounding puncture tract TR, a decrease in the circumference of the puncture tract is achieved through inflation of balloons 52 within tissue T, which temporarily increase the volume of the tissue, causing the tissue to swell into the puncture tract, thereby decreasing the circumference of the puncture tract. Balloons 52 may be made of fluid-impermeable elastic material, such as rubber.

In its deployment configuration, each balloon 52 is disposed around its associated needle 30, as shown in FIG. 7B. Accordingly, when tips 35 of needles 30 penetrate into tissue T, balloons 52 also are introduced into the tissue. Once needles 30 have been disposed within tissue T in the same manner as that described above with respect to FIGS. 5A-5C, a standard inflation source, e.g., a syringe (not shown), is fluidically coupled to inlet port 28 so that inflation fluid, such as air, water or saline, may be injected into injection manifold 16 for delivery to balloons 52 through needles 30 and apertures 32.

Inflation of balloons 52 affects a volumetric increase in tissue T that causes the tissue to swell into puncture tract TR, thereby decreasing the circumference of puncture P. If expandable member 24 is provided at the distal end of shaft 14, a proximal force may be applied to shaft 14, as discussed hereinabove, to engage expandable member 24 to inner vessel wall W', thereby-proximally deflecting tissue T as the tissue swells. After a period of time during which blood ceases to flow from puncture tract TR, balloons 52 may be deflated and retracted from tissue T along with needles 30 and shaft 14.

Alternatively, if expandable member 24 is not provided to facilitate determination of the maximum distal depth to which needles 30 may be translated within tissue T, radiopaque markers 37 disposed at the distal tip of needles 30 may be used along with conventional fluoroscopic techniques. As yet another alternative, the lengths of needles 30 may be selected so that the needles will not penetrate the vessel.

In a further alternative embodiment of device 10, injection port 28, injection lumen 31 and apertures 32 may be omitted. Rather than injecting a closure agent or inflation fluid into needles 30 via injection port 28 and manifold 16, needles 30 may be pre-coated with an inflammatory substance that will dissolve upon exposure to the fluids within tissue T, releasing the inflammatory substance to cause an inflammation response that swells the tissue into the puncture tract.

Figure 8:
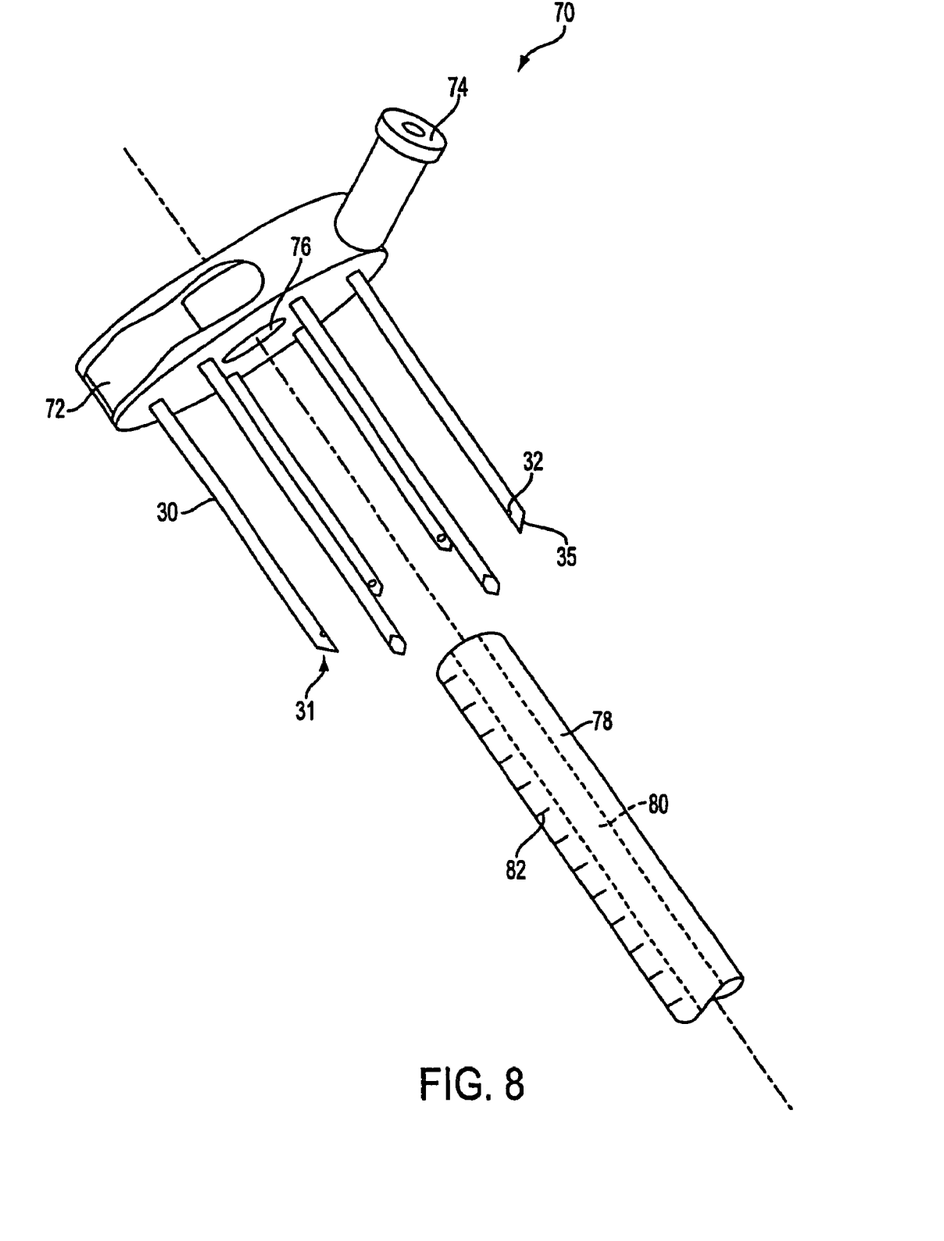
FIG. 8 is a schematic perspective cut-away view of an alternative embodiment of the present invention.

Referring now to FIG. 8, an alternative embodiment of the present invention is described, wherein device 70 may be provided comprising plurality of needles 30 disposed in fluid communication with manifold 72 having injection port 74 that may be fluidically coupled to a source of closure agent, e.g., one or more syringes (not shown). As with device 10, each needle 30 has injection lumen 31 in fluid communication with aperture 32 disposed on distal tip 35. Manifold 72 preferably is annularly shaped with central bore 76 that may be translatably disposed around optional centering shaft 78. While FIG. 8 shows an annular manifold having a circumferential array of needles, it will be evident to one of ordinary skill in the art that other shapes and configurations may be provided without departing from the scope of the invention.

Device 70 limits a maximum depth to which needles 30 may be advanced into tissue T by providing needles of a specified length that is not as long as the length of the puncture tract. Alternatively, the maximum depth may be limited by specifying the distance that needles 30 may extend beyond manifold 72. Preferably, when needles 30 are inserted to their maximum depth, manifold 72 abuts the exterior of the patient, i.e., the patient's skin. Such depth may, for example, be limited to less than 5 cm. This depth is provided only for the sake of illustration and alternative depths will be apparent to those of skill in the art. Limiting the depth to which needles 30 may be inserted into tissue T is expected to reduce a risk of inadvertent insertion of needles 30 into vessel V.

The apparatus optionally may comprise centering shaft 78 that may be translatably disposed within central bore 76 of manifold 72 and within puncture tract TR. Plurality of needles 30 may be advanced in unison with centering shaft 78 into tissue T and puncture tract TR, respectively, in which case centering shaft 78 optionally may be formed as an integral part of device 70. Alternatively, plurality of needles 30 may be advanced over centering shaft 78 after centering shaft 78 has already been disposed within puncture tract TR. Both embodiments center needles 30 for accurate penetration thereof into tissue T surrounding the puncture tract.

Centering shaft 78 may incorporate optional central lumen 80 that may be used to determine the depth of puncture tract TR so that an appropriate maximum depth to which the needles may be advanced or an appropriate length of needles 30 may be chosen. Specifically, centering shaft 78 may be inserted into puncture tract TR until blood from vessel V backbleeds into lumen 80. This indicates that the distal end of central shaft 78 (not shown) is disposed just proximal to vessel V, or, alternatively, that the distal end of central shaft 78 is disposed at the distal end of puncture tract TR. Indicia 82 disposed on the proximal end of central shaft 78 then may be noted to determine the depth of puncture tract TR, or alternatively the maximum depth/length of needles 30 that may be used to avoid inadvertent penetration of needles 30 into vessel V. Accordingly, the present invention preferably provides a multiplicity of needle lengths. Alternatively, the distance of needles 30 extending beyond manifold 72 may be adjustable.

As in the preceding embodiments, the closure agent may include a water swellable gel, collagen, an inflammatory substance, a saline bolus, and/or a granular slurry of a biocompatible substance. Alternatively, the closure agent may comprise a plurality of balloons affixed to the distal ends of needles 30 over apertures 32. Inflation fluid may be introduced into the balloons through injection port 74 and manifold 72.

Figure 9:
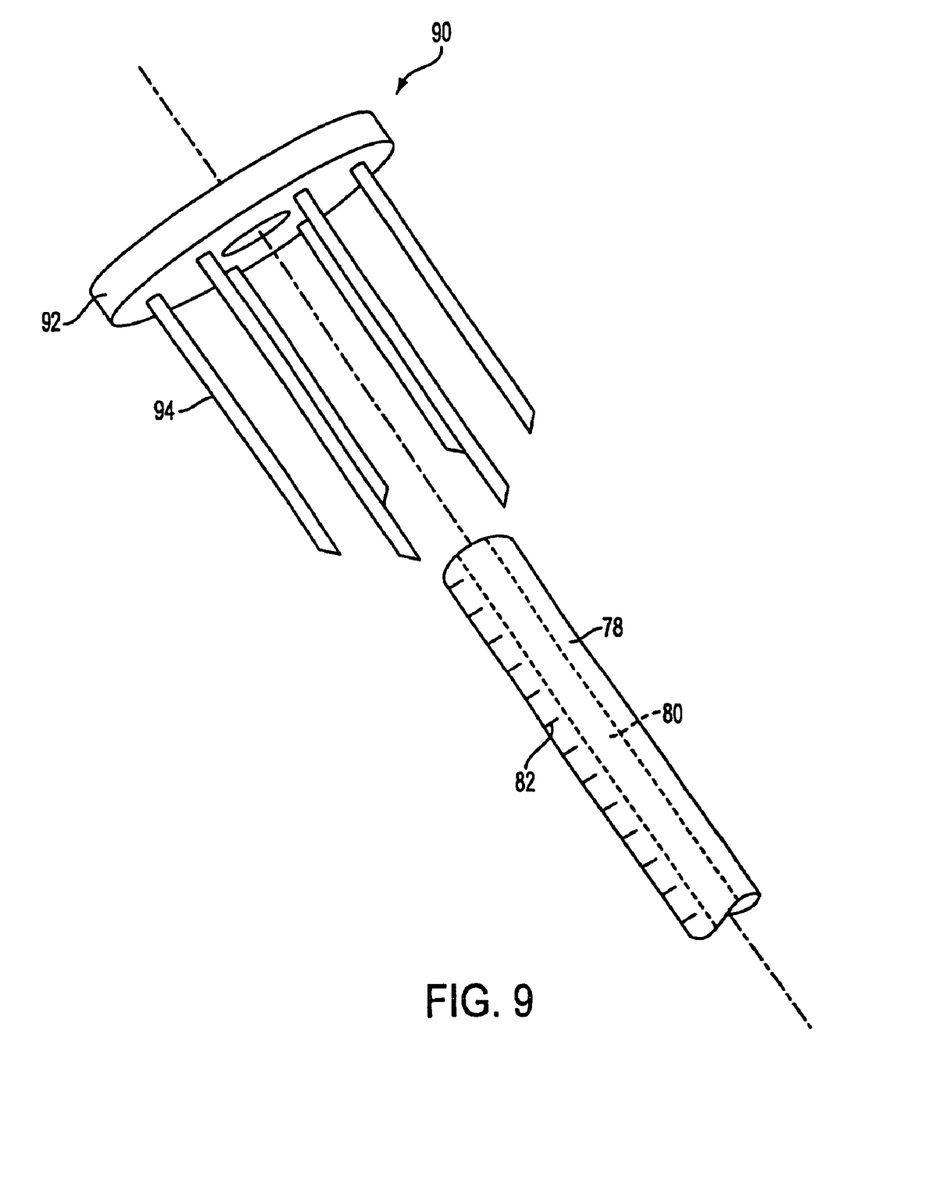
FIG. 9 is a schematic perspective view of another alternative embodiment of the present invention.

In a further alternative embodiment of the present invention, injection manifold 72 and injection port 74 may be omitted. Device 90 comprises solid housing 92 to which plurality of needles 94 are affixed. Device 90 also may comprise optional centering shaft 78 having central lumen 80 and indicia 82. Centering shaft 78 may be formed integrally with device 90 or may be provided as a separate element. As in the previous embodiment, centering shaft 78 may be used to align plurality of needles 84 with puncture tract TR, and central lumen 80 and indicia 82 may be used to determine the length of puncture tract TR and thereby the maximum length of needles 94 that may be used to avoid inadvertent penetration thereof into vessel V. Alternatively, the distance of needles 94 extending beyond housing 92 may be adjustable, thereby making the maximum depth to which the needles may be advanced into tissue T adjustable.

Device 90 differs from the previous embodiments in that needles 94 are solid, i.e. have no injection lumen. To deliver a closure agent to tissue T surrounding puncture tract TR, needles 94 are pre-coated with an inflammatory substance that dissolves within tissue T upon penetration thereof and exposure to the fluids therein. A resultant inflammation response swells tissue T into puncture tract TR, thereby closing puncture P.

While preferred illustrative embodiments of the present invention are described above, it will be apparent to one skilled in the art that various changes and modifications may be made therein without departing from the invention. For example, additional closure agents, per se known, will be apparent. The appended claims are intended to cover all such changes and modifications that fall within the true spirit and scope of the invention.

The invention claimed is:

1. An apparatus for sealing a puncture tract disposed within tissue, the apparatus comprising:
   a housing;
   a manifold having an inlet port and a central opening, the manifold slidably engaging with the housing and being configured to receive a closure agent;
   a shaft slidably disposed through the housing and the central opening of the manifold, the shaft having an expandable member disposed from a distal end of the shaft, the expandable member being configured to be disposed within the puncture tract to stabilize the tissue; and
   a plurality of needles mounted to the manifold, the plurality of needles being slidable with the manifold to extend from the housing, the plurality of needles configured to penetrate tissue surrounding the puncture tract to deliver the closure agent from the manifold into the tissue to thereby seal the puncture tract.

2. The apparatus of claim 1, wherein the expandable member is configured to be disposed within the puncture tract to stabilize the tissue during insertion of the plurality of needles.

3. The apparatus of claim 1, further comprising a stop configured to limit translation of the plurality of needles into the tissue.

4. The apparatus of claim 1, further comprising an actuator coupled to the plurality of needles for selective translation of the plurality of needles.

5. The apparatus of claim 1, wherein the manifold is configured to cooperate within a source of the closure agent, wherein the closure agent received in the manifold comprises a biodegradable substance.

6. The apparatus of claim 5, wherein the biodegradable substance is chosen from the group consisting of a water swellable gel, collagen, a saline bolus, a slurry of a biocompatible substance, and combinations thereof.

7. The apparatus of claim 1, wherein the manifold is configured to cooperate with a source of the closure agent, wherein the closure agent received in the manifold comprises an inflammatory substance that causes a localized inflammation response.

8. The apparatus of claim 7, wherein the inflammatory substance comprises copper sulfate.

9. The apparatus of claim 1, further comprising at least one balloon coupled to the plurality of needles, the at least one balloon being the closure agent.

10. The apparatus of claim 9, further comprising a radiopaque marker disposed adjacent to the distal tip of each one of the plurality of needles.

11. The apparatus of claim 1, wherein the plurality of needles are coated with the closure agent.

12. The apparatus of claim 1, wherein each one of the plurality of needles comprises a distal tip configured to penetrate the tissue, a distal aperture, and a lumen that couples the distal aperture to a source of closure agent.

13. The apparatus of claim 1 further comprising a radiopaque band disposed on the distal end of the shaft.

14. The apparatus of claim 1, wherein the manifold in fluid communication with the plurality of needles.

15. The apparatus of claim 1, wherein the expandable member has a deployed configuration configured for engagement with an interior surface of a vessel.

16. An apparatus for sealing a puncture tract disposed within tissue, the apparatus comprising:
    a housing having a base with a lumen;

a manifold having an inlet port and a central opening, the manifold slidably engaging with the housing and being configured to receive a closure agent;

a shaft disposed through the lumen of the housing and the central opening of the manifold, the shaft including a stop configured to cooperate with the base, the shaft having an expandable member disposed from a distal end of the shaft, the expandable member being configured to be disposed within the puncture tract to stabilize the tissue, the stop being configured to limit longitudinal movement of the manifold relative to the expandable member; and a plurality of needles mounted to the manifold, the plurality of needles being slidable with the manifold to extend from the housing, the plurality of needles configured to penetrate tissue surrounding the puncture tract to deliver the closure agent received from the manifold into the tissue, thereby sealing the puncture tract.

17. The apparatus of claim 16, wherein the expandable member is configured to be disposed within the puncture tract to stabilize the tissue during insertion of the plurality of needles.

18. The apparatus of claim 16, further comprising an actuator coupled to the plurality of needles for selective translation of the plurality of needles.

* * * * *